(12) United States Patent
Waytashek

(10) Patent No.: US 8,150,515 B2
(45) Date of Patent: Apr. 3, 2012

(54) FUSEABLE CATHODE PLATE FOR ELECTROLYTIC CAPACITOR

(75) Inventor: Brian V. Waytashek, Lino Lakes, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 460 days.

(21) Appl. No.: 12/409,772

(22) Filed: Mar. 24, 2009

(65) Prior Publication Data

US 2009/0248093 A1     Oct. 1, 2009

Related U.S. Application Data

(60) Provisional application No. 61/039,914, filed on Mar. 27, 2008.

(51) Int. Cl.
*A61N 1/00*     (2006.01)

(52) U.S. Cl. .......................................................... 607/29
(58) Field of Classification Search ...................... 607/29
See application file for complete search history.

(56) References Cited

U.S. PATENT DOCUMENTS 5,224,261 A * 7/1993 Morrill, Jr. ...................... 29/623
5,432,672 A * 7/1995 Kuriyama et al. ............. 361/534

* cited by examiner

*Primary Examiner* — George Manuel
(74) *Attorney, Agent, or Firm* — Schwegman, Lundberg & Woessner, P.A.

(57) ABSTRACT

An electrolytic capacitor is constructed in a manner to provide a fusing capability and welded connections between the cathode plates. Each cathode plates has a notch at its periphery within which is an extending leg over which a weldable metallic clip is fitted in order to reduce the area of the cathode plate through which current is conducted to reach the clip and form a fusible link.

15 Claims, 3 Drawing Sheets

FUSEABLE CATHODE PLATE FOR ELECTROLYTIC CAPACITOR

CROSS-REFERENCE TO RELATED APPLICATION

This application claims the benefit of U.S. Provisional Application No. 61/039,914, filed on Mar. 27, 2008, under 35 U.S.C. §119(e), which is hereby incorporated by reference.

FIELD OF THE INVENTION

This invention relates to capacitors and methods for their construction. In particular, the invention pertains to capacitors used in implantable cardiac rhythm management devices such as cardioverter/defibrillators and pacemakers.

BACKGROUND

Implantable cardiac rhythm management devices, including pacemakers and implantable cardioverter/defibrillators (ICDs), are devices used to treat abnormalities of heart rhythm. Pacemakers, for example, treat bradycardia (i.e., a heart rate that is too slow) by delivering pacing pulses to the heart at appropriate times, while ICDs terminate fibrillation by delivering a defibrillation shock pulse to the heart. Such devices containing pulse generating circuitry for delivering pacing or shock pulses that is enclosed by a housing and connected by leads to electrodes disposed in or near the heart. Many cardiac rhythm management devices incorporate both ICD and pacemaker functionality in the same device.

Most cardiac rhythm management devices use a capacitive discharge circuit to deliver either pacing or shock pulses to the heart. Owing to their high energy density and ability to withstand high voltages, electrolytic capacitors are used in these devices. An electrolytic capacitor is a layered structure that includes a metal anode plate with an insulating oxide layer formed on its surface for constituting a dielectric, a metal cathode plate, and an electrolyte impregnated in a separator between the two plates. The metal used for the anode and cathode plates is usually aluminum or tantalum. A capacitor is thereby formed from the capacitance between the negatively charged electrolyte and the positively charged anode plate with the oxide layer acting as a dielectric. A stacked-type electrolytic capacitor generally includes a stack of flat capacitive elements, with each element including a paper separator between two sheets of aluminum, one serving as an anode plate and the other as a cathode plate. In a stacked-type of aluminum electrolytic capacitor, anode and cathode plates (also referred to as coupons) are cut from aluminum sheets in a shape designed to conform to a capacitor case. The capacitive elements are connected together in parallel to provide a total capacitance.

DETAILED DESCRIPTION

Figure 1:
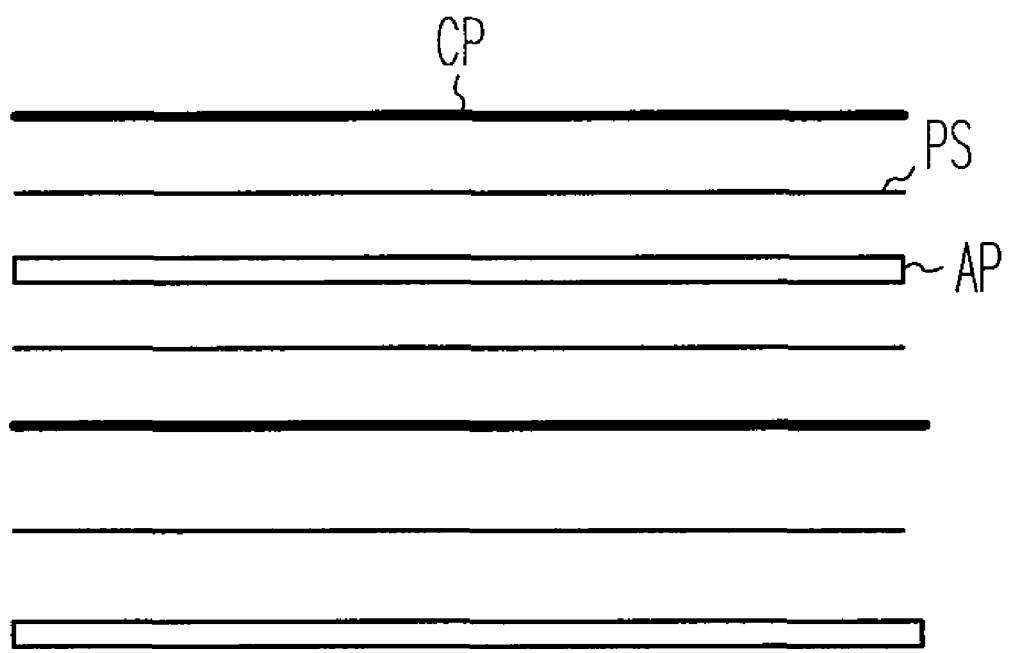
FIG. 1 shows a cross-sectional schematic of an electrolytic capacitor in a stacked configuration.

FIG. 1 shows a cross-sectional schematic of an electrolytic capacitor in a stacked configuration. The capacitor is made up of a plurality of capacitive elements that are stacked on one another and contained within a housing, with each capacitive element being a layered structure capacitor as described above. The anode plates AP are stacked on the cathode plates CP in alternate fashion with a paper separator PS interposed between each anode plate and each cathode plate. The paper separators are impregnated with a liquid electrolyte that allows current flow between the anode and cathode plates. The anode plates have oxide layers formed on both sides so that each side of the anode plate together with the adjacent electrolyte constitutes a capacitive element. The cathode plates are electrically connected in common to a negative terminal, while the anode plates are electrically connected in common to a positive terminal. The individual capacitive elements of the capacitor are thus connected in parallel to give a total capacitance.

Figure 2:
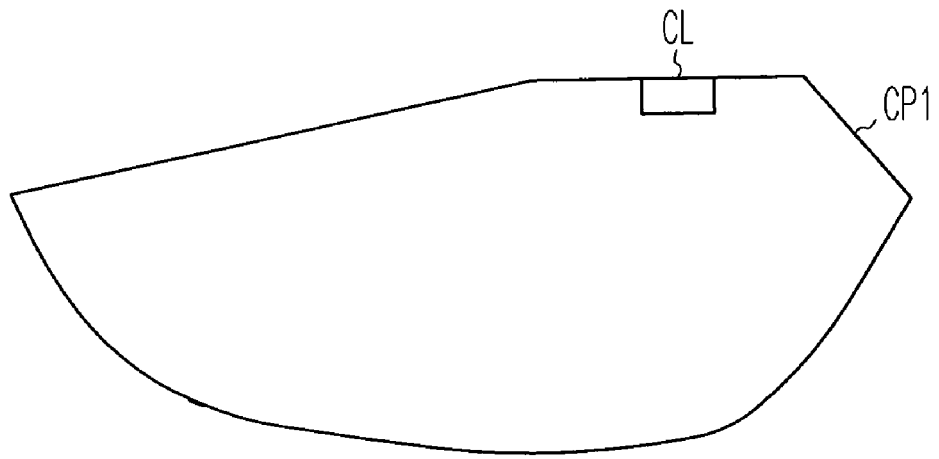
FIG. 2 shows an exemplary cathode plate.

The anode plates may be constructed with unoxidized portions that may be welded together to make the electrical connections between the anode plates of the capacitor. The cathode plates, however, are much thinner than the anode plates, and this makes it problematic to directly weld the cathode plates together. For this reason, a metallic clip may be attached to the periphery of each cathode plate (e.g., by crimping or staking). The clips may then be welded together to electrically connect the cathode plates together. FIG. 2 shows an exemplary cathode plate CP1. The shape of the cathode plate is dictated by the shape of housing in which the stacked capacitive elements are to be contained. In order to electrically connect the plurality of cathode plates in the stack to one another, a metallic clip or tab CL is shown as being attached to the edge of the cathode plate CP1. The clip CL fits over the edge of the cathode plate CP1 and may be attached thereto by staking or crimping. After the plurality of capacitive elements are stacked, the corresponding plurality of clips CL may then be welded together and connected to a terminal in order to establish the parallel connection.

A problem that arises with electrolytic capacitors is the occurrence of an arc event in one of the capacitive elements (i.e., in one of the anode-cathode cells of the stack). Such an arc event may create a short circuit within the particular capacitive element that, since all of the capacitive elements are connected in parallel, prevents the capacitor from reaching its rated voltage and prevents the damaged capacitive element from being reformed. It is therefore desirable for an electrolytic capacitor to have a built-in fuse for each anode-cathode cell that makes up the capacitor. When an arc event occurs, all the stored energy of the capacitor contains is sent through the single cathode layer that contained the arc event (instead of being distributed among all of the cathode interconnections as during a normal discharge). If each cathode were to have a built-in fuse that open circuits when the current reaches a certain level in the interconnection path between the cathode plates, however, an arc event in one of the anode-cathode cells would fuse that cathode open and isolate the damaged section of the capacitor. The remaining portion of the capacitor would then be able to charge and discharge normally, although at a reduced energy level.

Figure 3:
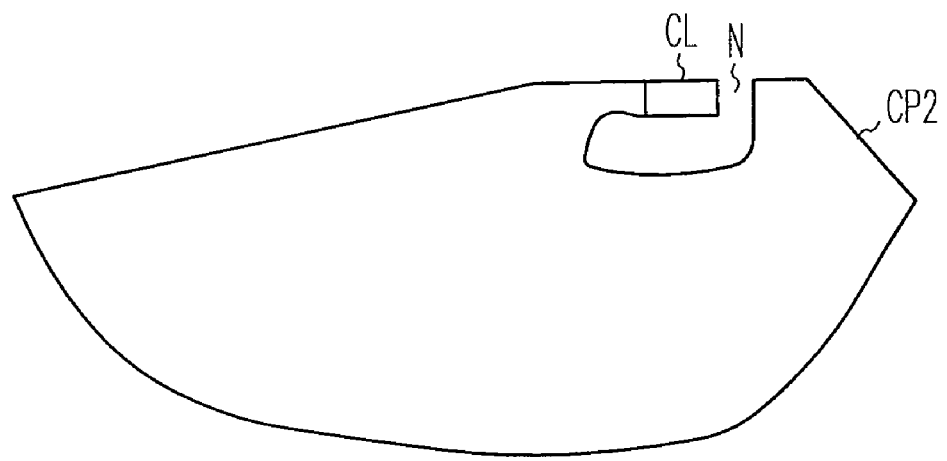
FIG. 3 shows an exemplary cathode plate designed to allow fusing capability.

FIG. 3 illustrates a cathode plate CP2 that is constructed in a manner to provide a fusing capability and obtain the advantages described above. The cathode plate CP2 has a notch at its periphery within which is an extending leg L of the cathode plate over which the clip is fitted in order to reduce the area of the cathode plate through which current is conducted to reach the clip and form a fusible link. In this embodiment, the notch N is an L-shaped notch that leaves a peripheral portion of the cathode plate as the extending leg. By reducing an area of the conduction path in the cathode plate through which current flows to the clip, the current density in that area may be increased to such an extent that the area will open circuit if a certain current amplitude is exceeded. For example, a dimension of the extending leg of the cathode plate within the notch is selected so that the fusible link open circuits at approximately 30 amps. In a particular embodiment, the anode and cathode plates are made of aluminum, the cathode plates are approximately 1 mil thick, and the extending legs are rectangular in shape with a width less than 60 mils.

Figure 4:
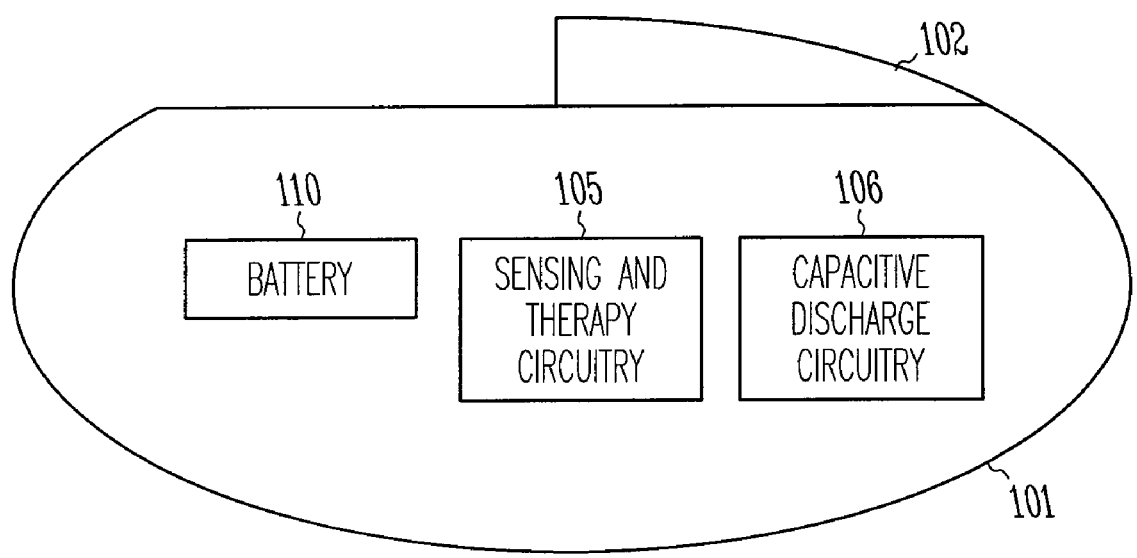
FIG. 4 depicts the layout of an implantable cardiac rhythm management device.

FIG. 4 shows a typical layout of an implantable cardiac rhythm management device. The housing 101 is usually made of titanium or other biocompatible metal and contains the electronic components necessary for sensing cardiac activity and delivering electrostimulation to the heart. These components include sensing and therapy circuitry 105, a capacitive discharge circuit 106 that include one or more electrolytic capacitors constructed as described above, and a battery 110. One or more leads with electrodes for disposition near the heart are connected to the sensing and therapy circuitry contained within the housing by means of a header 102 which has feedthroughs located therein for routing the leads to the appropriate internal components.

The invention has been described in conjunction with the foregoing specific embodiments. It should be appreciated that those embodiments may also be combined in any manner considered to be advantageous. Also, many alternatives, variations, and modifications will be apparent to those of ordinary skill in the art. Other such alternatives, variations, and modifications are intended to fall within the scope of the following appended claims.

What is claimed is:

1. An electrolytic capacitor, comprising:
    a plurality of planar metallic anode plates with an insulating oxide layer formed on both surfaces of each anode plate for constituting a dielectric;
    a plurality of electrolyte impregnated separators;
    a plurality of planar metallic cathode plates;
    wherein the capacitor is constructed as a stacked structure of alternating anode and cathode plates with an electrolyte impregnated separator interposed between each anode and cathode plate;
    a clip fitted over a peripheral portion of each cathode plate, the clips being welded together to electrically connect the cathode plates in common; and,
    wherein each cathode plate has a notch at its periphery within which is an extending leg of the cathode plate over which the clip is fitted in order to reduce the area of the cathode plate through which current is conducted to reach the clip and form a fusible link.

2. The capacitor of claim 1 wherein a dimension of the extending leg of the cathode plate within the notch is selected so that the fusable link open circuits at approximately 30 amps.

3. The capacitor of claim 1 wherein:
    the anode and cathode plates are made of aluminum;
    the cathode plates are approximately 1 mil thick; and,
    the extending legs are rectangular in shape with a width less than 60 mils.

4. The capacitor of claim 1 wherein the notch of each cathode plate is an L-shaped notch that leaves a peripheral portion of the cathode plate as the extending leg.

5. The capacitor of claim 1 wherein the anode plates are connected by welding portions of the anode plates together to electrically connect the anode plates in common.

6. A method for constructing an electrolytic capacitor, comprising:
    providing a plurality of planar metallic anode plates with an insulating oxide layer formed on both surfaces of each anode plate for constituting a dielectric;
    providing a plurality of electrolyte impregnated separators;
    providing a plurality of planar metallic cathode plates;
    constructing the capacitor as a stacked structure of alternating anode and cathode plates with an electrolyte impregnated separator interposed between each anode and cathode plate;
    fitting a clip over a peripheral portion of each cathode plate, the clips being welded together to electrically connect the cathode plates in common; and,
    wherein each cathode plate has a notch at its periphery within which is an extending leg of the cathode plate over which the clip is fitted in order to reduce the area of the cathode plate through which current is conducted to reach the clip and form a fusible link.

7. The method of claim 6 wherein a dimension of the extending leg of the cathode plate within the notch is selected so that the fusable link open circuits at approximately 30 amps.

8. The method of claim 6 wherein:
    the anode and cathode plates are made of aluminum;
    the cathode plates are approximately 1 mil thick; and,
    the extending legs are rectangular in shape with a width less than 60 mils.

9. The method of claim 6 wherein the notch of each cathode plate is an L-shaped notch that leaves a peripheral portion of the cathode plate as the extending leg.

10. The method of claim 6 further comprising connecting the anode plates by welding portions of the anode plates together to electrically connect the anode plates in common.

11. An implantable cardiac rhythm management device, comprising:
    an implantable housing;
    sensing and therapy circuitry disposed within the implantable housing;
    a capacitive discharge circuit that includes one or more electrolytic capacitors, wherein each capacitor comprises:
    a plurality of planar metallic anode plates with an insulating oxide layer formed on both surfaces of each anode plate for constituting a dielectric;
    a plurality of electrolyte impregnated separators;
    a plurality of planar metallic cathode plates;
    wherein the capacitor is constructed as a stacked structure of alternating anode and cathode plates with an electrolyte impregnated separator interposed between each anode and cathode plate;
    a clip fitted over a peripheral portion of each cathode plate, the clips being welded together to electrically connect the cathode plates in common; and,
    wherein each cathode plate has a notch at its periphery within which is an extending leg of the cathode plate over which the clip is fitted in order to reduce the area of the cathode plate through which current is conducted to reach the clip and form a fusible link.

12. The device of claim 11 wherein a dimension of the extending leg of the cathode plate within the notch is selected so that the fusable link open circuits at approximately 30 amps.

13. The device of claim 11 wherein:
    the anode and cathode plates are made of aluminum;
    the cathode plates are approximately 1 mil thick; and,
    the extending legs are rectangular in shape with a width less than 60 mils.

14. The device of claim 11 wherein the notch of each cathode plate is an L-shaped notch that leaves a peripheral portion of the cathode plate as the extending leg.

15. The device of claim 11 wherein the anode plates are connected by welding portions of the anode plates together to electrically connect the anode plates in common.

\* \* \* \* \*